United States Patent [19]

Nozaki et al.

[11] Patent Number: 5,395,542
[45] Date of Patent: Mar. 7, 1995

[54] LIQUID DETERGENT COMPOSITION

[75] Inventors: Toshio Nozaki, Chiba; Akira Fujiu, Wakayama; Yasushi Kajihara, Kasukabe, all of Japan

[73] Assignee: Kao Corporation, Tokyo, Japan

[21] Appl. No.: 93,136

[22] Filed: Jul. 19, 1993

Related U.S. Application Data

[63] Continuation of Ser. No. 818,560, Jan. 9, 1992, abandoned.

[30] Foreign Application Priority Data

Jan. 23, 1991 [JP] Japan .................................. 3-022912
Nov. 13, 1991 [JP] Japan .................................. 3-297267

[51] Int. Cl.$^6$ ........................... C11D 7/36; C11D 3/36
[52] U.S. Cl. ................................. 252/174.16; 252/90; 252/135; 252/173; 252/DIG. 5; 252/DIG. 13; 252/DIG. 14
[58] Field of Search ............... 252/174.16, 135, 90, 252/132, 173, 542, 545, 546, 548, DIG. 25, DIG. 13, DIG. 14

[56] References Cited

U.S. PATENT DOCUMENTS

| | | | |
|---|---|---|---|
| 4,018,696 | 4/1977 | Hellster et al. | 252/89 R |
| 4,139,485 | 2/1979 | Imakawa et al. | 252/135 |
| 4,707,292 | 11/1987 | Sano et al. | 252/174.16 |
| 5,062,989 | 11/1991 | Kamegai et al. | 252/174.17 |

FOREIGN PATENT DOCUMENTS 0231997 8/1987 European Pat. Off.
2027047 2/1980 United Kingdom.

*Primary Examiner*—P. Achutamurthy
*Attorney, Agent, or Firm*—Oblon, Spivak, McClelland, Maier & Neustadt

[57] ABSTRACT

A liquid detergent composition containing the following components (a) and (b) at a proportion of (a)/[(a)+(b)] of 0.4 –1:

(a) phosphoric ester of the following formula (1)

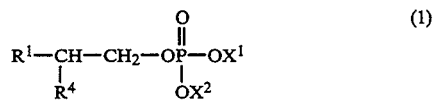

where $R^1$ is a $C_8$–$C_{12}$ linear hydrocarbon group, $R^4$ is a $C_1$–$C_4$ linear hydrocarbon group and $X^1$ and $X^2$ are, independently, a potassium atom or a hydrogen atom; and (b) phosphoric ester of the following formula (2):

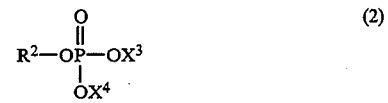

wherein $R^2$ is a $C_{11}$–$C_{15}$ linear hydrocarbon group and $X^3$ and $X^4$ are, independently, a potassium atom or a hydrogen atom.

14 Claims, No Drawings

LIQUID DETERGENT COMPOSITION

This application is a continuation of application Ser. No. 07/818,560, filed on Jan. 9, 1992, now abandoned.

BACKGROUND OF THE INVENTION

1. Field of the Invention

This invention relates to a liquid detergent composition, and more particularly to a liquid detergent composition which is suitable for cleansing the skin and the hair, has good foamability, gives users a pleasant feel upon use, is stable and applicable to finger-push type pump containers.

2. Discussion of the Background

Among liquid detergent compositions which are applied to the body, shampoos for the hair have conventionally been widely used. Recently, liquid body shampoos have become familiar to users instead of soaps because of their properties of agreeable touch and ease of use.

As a component of detergent compositions, phosphate surfactants, which are classified as anionic surfactants, are used because they are mild to the hair and the skin. Among these phosphate surfactants, alkali metal salts of the surfactants have a high Krafft point, and are difficult to liquefy. This drawback has been overcome by converting the surfactants into alkanolamine salts to lower the Krafft point and to liquefy them. However, when converted into alkanolamine salts, foam producing ability (hereinafter referred to as foamability) is significantly deteriorated, which has left much room for improvements to provide satisfactory surfactant components for detergents.

Furthermore, phosphate surfactants as a component of detergent compositions give disagreeable rough and frictional feel when used with hard water.

Moreover, when a liquid detergent composition containing an alkanolamine salt of a phosphate surfactant is charged into a finger-push type pump container and used repeatedly, the gelled or solidified composition plugs the nozzle of the container, causing objectionable appearance and ejection of the composition in a wrong direction upon use.

SUMMARY OF THE INVENTION

Accordingly, one object of the present invention is to provide liquid detergent compositions containing a phosphate surfactant which maintain good characteristics of the surfactant, have excellent foamability, are stable, provide agreeable feel upon use, and are suitably applicable for finger-push type pump containers.

This and other objects which will become apparent from the following specification have been achieved by the present detergent composition which contains phosphate surfactants (a) and (b) at a specified ratio in a stable liquid state, and provides an agreeable feel upon use, is mild to the skin and is suitable for use with a finger-push type pump container because it does not readily solidify.

DETAILED DESCRIPTION OF THE PREFERRED EMBODIMENTS

This invention provides a liquid detergent composition comprising the following components (a) and (b):

(a) one or more compounds of formula (1):

$$R^1-\underset{\underset{R^4}{|}}{CH}-CH_2-\underset{\underset{OX^2}{|}}{\overset{\overset{O}{\|}}{O-P}}-OX^1 \qquad (1)$$

where $R^1$ is a $C_8-C_{12}$ linear hydrocarbon group, $R^4$ is a $C_1-C_4$ linear hydrocarbon group and $X^1$ and $X^2$ are, independently, a potassium atom or a hydrogen atom;

(b) one or more compounds of formula (2):

$$R^2-\underset{\underset{OX^4}{|}}{\overset{\overset{O}{\|}}{O-P}}-OX^3 \qquad (2)$$

where $R^2$ is a $C_{11}-C_{15}$ linear hydrocarbon group and $X^3$ and $X^4$ are, independently, a potassium atom or a hydrogen atom, the proportion by weight, $(a)/[(a)+(b)]$ being 0.4 to 1.

Referring to formula (1) of component (a), examples of group $R^1$ include a $C_8-C_{12}$ linear alkyl groups or alkenyl groups, in particular, linear alkyl groups such as octyl, nonyl, decyl, undecyl and dodecyl. Preferable examples of $R^4$ are methyl and ethyl, and methyl is particularly preferred.

Referring to formula (2) of component (b), examples of group $R^2$ include $C_{11}-C_{15}$ alkyl groups or alkenyl groups, in particular, linear alkyl groups such as undecyl, dodecyl, tridecyl, tetradecyl and pentadecyl.

The proportion of the components (a) and (b) to be incorporated into the composition of the present invention is in the following range:

$(a)/[(a)+(b)]=0.4-1$.

A value less than 0.4 indicates a high Krafft point for the composition indicating an unstable composition and should be avoided. Preferably, the proportion ranges from 0.50–0.90.

Components (a) and (b) are salts of phosphoric esters and are obtained, for example, by reacting an aliphatic alcohol with phosphoric anhydride or phosphorus oxychloride, followed by neutralization with a basic potassium salt, such as KOH. The aliphatic alcohol, examples of which include linear alcohols and branched alcohols, may be used singly or as a mixture. DIADOL 115L (product of Mitsubishikasei Co.) and DOBANOL 23I (product of Mitsubishiyuka Co.), which are commercially available alcohols, are mixtures of linear alcohols and 2-alkyl branched alcohols, and are useful to provide a mixture of salts of phosphoric esters which meet the requirement of $(a)/[(a)+(b)]$ being 0.4–1.

The combined amount of components (a) and (b) to be incorporated into the present liquid detergent composition is 5–60% by weight, preferably 10–40% by weight, of the total composition.

The present liquid detergent composition may optionally contain other compatible ingredients which are generally used in this field. Such ingredients include moisturizers such as propylene glycol, glycerol and sorbitol; viscosity modifiers such as methylcellulose, polyoxyethylene glycol distearate and ethanol; germicides such as triclosan and triclocarban; anti-inflammatory agents such as potassium glycyrrhizate and tocopherol acetate; antidandruff agents such as zinc pyrithione and octopyrox; antiseptics such as methylparaben and butylparaben; pearly lustre-imparting agents; perfumes;

colorants; UV absorbers and antioxidants. They can be incorporated in any amounts which do not impede the effects of the inventive compositions.

Furthermore, the liquid detergent compositions of this invention may optionally contain suitable amounts of various surfactants other than described above, so long as they do not impede the effects of the inventive compositions. Examples of other surfactants include sulfates or sulfonates (anionic surfactants) such as alkyl sulfates and polyoxyethylene alkyl sulfates; sulfosuccinates; taurates; isethionates; alpha-olefinsulfonates; carboxylates such as aliphatic soaps, ether carboxylic surfactants and acylated amino acid surfactants. Among them, aliphatic surfactants and isethionate surfactants are especially preferred from the viewpoint of texture and foamability.

Referring to amphoteric surfactants, examples useful in this invention include carbobetaines, sulfobetaines and imidazolinium betaines. In particular, hydroxypropyl-sulfobetaine and demineralized secondary imidazolinium betaine are preferred.

Referring to nonionic surfactants, examples useful in this invention include polyoxyalkylene adducts, polyoxypropylene-polyoxyethylene adducts, amine oxides, mono- or di-ethanolamides, sorbitan fatty acid esters, glyceryl fatty acid esters, sucrose fatty acid esters, alkyl saccharides, and N-polyhydroxyalkyl fatty acid amides. Among them, most preferred are amine oxides, diethanolamides and alkyl saccharides.

Referring to cationic surfactants, examples useful in this invention include mono- or di- alkyl adduct type quaternary ammonium salts having a linear or branched alkyl group, where the alkyl group may or may not contain alkylene oxide units. In particular, $C_{12}-C_{16}$ linear monoalkyl quaternary ammonium salts and quaternary ammonium salts having $C_{20}-C_{28}$ branched alkyl groups are preferred.

The above-mentioned optional surfactants are used singly or in combination. Preferred amounts are 2–40% by weight, more preferably 5–25% by weight of the total composition. The proportion to the combined amounts of components (a) and (b) and that of the optional surfactants is preferably 5:1–1:5, and more preferably, 3:1–1:2.

The liquid detergent compositions of this invention are prepared by known processes. The pH of the compositions is desirably adjusted to 5–10, more preferably, 6–8.5 with KOH.

The liquid detergent composition of this invention have the good feeling when used, excellent foamability, and prolonged stability. Accordingly, they are useful as shampoos, body shampoos, and further, detergents for the kitchen use and the like which directly contact the skin for a long time. Also, the compositions are suited for use with hard water, giving little or no frictional feel or rough touch upon use. Moreover, since the compositions are not gelled or solidified, they may be used in a container having a finger-push pump.

Other features of the invention will become apparent in the course of the following descriptions of exemplary embodiments which are given for illustration of the invention and not intended to be limiting thereof.

EXAMPLES

Reference Example 1

Phosphoric esters (A) to (F) (before neutralization) shown in Table 1 were prepared using various starting alcohols. The carbon numbers in the table indicate the total carbon numbers of the alkyl group of the phosphoric esters.

TABLE I

| Starting Alcohols | Phosphoric esters | | |
|---|---|---|---|
| | Carbon Number of Alkyl Group | (a)/[(a) + (b)] | Identification of composition |
| DIADOL 115L (product of Mitsubishi-kasei Co.) | Mixture of C11, C13 and C15, See *1 | 0.53 | (A) |
| DOBANOL 23I (product of Mitsubishi-yuka Co.) | Mixture of C12 and C13, See *2 | 0.90 | (B) |
| DOVANOL 23I (product of Mitsubishi-yuka Co.) | Mixture of C12 and C13, See *2 | 0.38 | (C) |
| $C_6H_{13}\underset{\underset{C_8H_{17}}{\mid}}{C}HCH_2OH$ | 16 | — | (D) |
| $C_4H_9\underset{\underset{C_6H_{17}}{\mid}}{C}HCH_2OH$ | 12 | — | (E) |
| Lauryl Alcohol | 12 | 0 | (F) |

*1: Proportion by weight of $C_{11}:C_{13}:C_{15}$ is 47:31:22.
*2: Proportion by weight of $C_{12}:C_{13}$ is 43:57.

Example 1

Liquid detergent compositions were prepared using phosphoric esters (A) to (F) prepared in Reference Example 1. They were evaluated in terms of the Krafft point, stability in the liquid state and the volume of foams (40° C. and 20° C.) according to the following methods. The results are shown in Table 2.

Feel upon use of the inventive composition Nos. 1–4 and comparative composition No. 4 when used with hard water was also evaluated. The results are shown in Table 2.

Krafft point:

A twenty-fold diluted solution of each of the liquid detergent compositions was provided for measurement by conventional means.

Stability in the liquid state:

The liquid detergent compositions were evaluated in terms of the liquidity at 0° C. by the naked eye according to the criteria below.

Criteria:
O: Transparent liquid
X: Crystals deposited, floating or sedimentated

Foam Volumes:

A ten-fold diluted aqueous solution of each of the liquid detergent compositions was provided for the test. 100 ml (temperature of the solution: 20° C., 40° C.) of the solution was placed in a messcylinder. Stirring blades were placed in the solution and stirred (1,000 rpm, reversed every 5 seconds). The volume of foams generated 30 seconds after the stirring was started was measured.

A: 200 ml or more (good)
B: 200–150 ml (fair)
C: less than 150 ml (not good)

Feel upon use with hard water:

A panel consisting of 10 women washed their hands with invention composition Nos. 1–4 (See Table 2) and comparative composition No. 4, under the conditions of 40° C. water temperature and 10° DH hardness of water, and sensually evaluated them according to the following criteria:

Criteria: Frictional feel during rinsing
A: No frictional feeling
B: Slight frictional feeling
C: Very frictional feeling Rough and Dry feel after dried
A: No rough/dry feeling
B: Slight rough/dry feeling
C: Rough/Dry feeling The results are shown in Table 2 as averages of evaluations.

amine salt of lauryl phosphate solidified for the most part after the test period of 120 hours.

TABLE 3

|  | Aqueous solution of triethanolamine salt of lauryl phosphate | Aqueous solution of potassium salt of phosphoric ester (A) |
|---|---|---|
| Hardness of gel (g/cm$^2$) | 1160 | 30 |

Example 3

The resistivity to hard water of the phosphoric ester used in the present invention was examined with the parameter of scum (calcium salt) generation in hard water. Namely, an aqueous solution of a potassium salt of lauryl phosphate (acid concentration: 1%, pH 7.6) and an aqueous solution of a potassium salt of phosphoric ester (A) (acid concentration: 1%, pH 7.6) were provided, and 0.5 ml of each was diluted with 4.5 ml of identical hard water and stirred for 10 seconds. The turbidity of the liquids was measured with a turbidity meter (TURBIDIMETER MODEL T-2600DX, manufactured by Tokyo Denshoku K.K.). The results are shown in Table 4.

The aqueous solution of the potassium salt of phosphoric ester.(A) used in the present invention exhibited excellent resistivity against hard water when compared to the aqueous solution of the potassium salt of lauryl phosphate.

TABLE 2

|  | Invention compositions* | | | | Comparative compositions* | | | | | |
|---|---|---|---|---|---|---|---|---|---|---|
|  | 1 | 2 | 3 | 4 | 1 | 2 | 3 | 4 | 5 | 6 |
| Potassium salt of phosphoric ester (A) | 20 | 30 | 40 |  |  |  |  |  |  |  |
| Potassium salt of phosphoric ester (B) |  |  |  | 30 |  |  |  |  |  |  |
| Potassium salt of phosphoric ester (C) |  |  |  |  | 30 |  |  |  |  |  |
| Potassium salt of phosphoric ester (D) |  |  |  |  |  | 30 |  |  |  |  |
| Potassium salt of phosphoric ester (E) |  |  |  |  |  |  | 30 |  |  |  |
| Potassium salt of phosphoric ester (F) |  |  |  |  |  |  |  | 30 |  |  |
| Sodium salt of phosphoric ester (A) |  |  |  |  |  |  |  |  | 30 |  |
| Triethanolamine salt of Phosphoric ester (A) |  |  |  |  |  |  |  |  |  | 30 |
| Purified water |  |  |  |  | ←Balance→ | | | | | |
| pH | 7.0 | 7.5 | 8.0 | 7.5 | 7.5 | 7.5 | 7.5 | 7.5 | 7.5 | 7.5 |
| Krafft point (°C.) | <0 | <0 | <0 | <0 | 11 | <0 | <0 | 19 | 23 | <0 |
| Liquid stability | O | O | O | O | X | O | O | X | X | O |
| Foam volume (40° C.) | A | A | A | A | A | C | C | A | A | C |
| Foam volume (20° C.) | A | A | A | A | A | C | C | B | C | C |
| Frictional feeling during rinsing | A | A | A | A | — | — | — | C | — | — |
| Rough/dry feeling after dried | A | A | A | A | — | — | — | B | — | — |

*(% by weight)

Example 2

Readiness or hardness of solidification of the phosphoric esters to be used in the liquid detergent compositions of this invention was also studied. An aqueous solution of triethanolamine salt of lauryl phosphate (acid concentration: 15%, pH 7.6) and an aqueous solution of the potassium salt of phosphoric ester (A) prepared in Reference Example 1 (acid concentration: 15%, pH 7.6) were separately placed in glass bottles, and allowed to stand at 20° C., relative humidity 60% for 120 hours. The hardness of the gel generated at the liquid surface was measured with a rheometer (NRM-2010J-CW, manufactured by Fudo Kogyo K.K.) The results are shown in Table 3. The aqueous solution of the potassium salt of phosphoric ester (A), which is used in the inventive compositions maintained the liquid state, whereas the aqueous solution of the triethanol-

TABLE 4

|  | Aqueous solution of potassium salt of lauryl phosphate | Aqueous solution of potassium salt of phosphoric ester (A) |
|---|---|---|
| Scum generation in hard water (ppm) | | |
| 10DH | 560 | 80 |
| 20DH | 640 | 120 |

Example 4

A transparent liquid detergent composition (pH 7.5) was prepared according to the following formulation.

| (1) Potassium salt of phosphoric ester (A) | 35 wt. % |
|---|---|
| (2) Perfume | 0.5 wt. % |
| (3) Ethanol | 3 wt. % |
| (4) Dibutyl hydroxytoluene | 0.1 wt. % |

| (5) Water | balance |

Water (5) was heated, into which ingredient (1) was dissolved. After cooling, ingredients (2) to (4) were added to obtain a transparent liquid detergent composition (pH 7.5). The obtained detergent composition was used for washing the skin and the hair. It was revealed that the composition was mild to the skin, produced rich foams, and gave users refreshing and nice feeling upon use.

Obviously, numerous modifications and variations of the present invention are possible in light of the above teachings. It is therefore to be understood that within the scope of the appended claims, the invention may be practiced otherwise than as specifically described herein.

What is claimed is:

1. A liquid detergent composition consisting essentially of the following components (a), (b) and (c):

(a) a compound of formula (1):

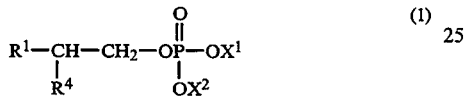

wherein $R^1$ is a $C_8$–$C_{12}$ linear hydrocarbon group, $R^4$ is a $C_1$–$C_4$ linear hydrocarbon group and $X^1$ and $X^2$ are, independently, a potassium atom or a hydrogen atom;

(b) a compound of formula (2):

wherein $R^2$ is a $C_{11}$–$C_{15}$ linear hydrocarbon group and $X^3$ and $X^4$ are, independently, a potassium atom or a hydrogen atom;

(c) a surfactant selected from the group consisting of the following surfactants (1), (2), (3) and (4):
   (1) an anionic surfactant selected from the group consisting of alkyl sulfate, polyoxyethylene alkyl sulfate, sulfosuccinate, taurate, isethionate, alphaolefinsulfonate, aliphatic soap, ethercarboxylic surfactant and acylated amino acid surfactant;
   (2) an amphoteric surfactant selected from the group consisting of carbobetaine, sulfobetaine and imidazolinium betaine;
   (3) a nonionic surfactant selected from the group consisting of polyoxyalkylene adduct, polyoxypropylene-polyoxyethylene adduct, amine oxide, mono or di-ethanolamide, sorbitan fatty acid ester, glyceryl fatty acid ester, sucrose fatty acid ester, alkyl saccharide, and N-polyhydroxyalkyl fatty acid amide; and
   (4) a cationic surfactant which is mono- or di-alkyl adduct quaternary ammonium salt having a linear or branched alkyl group, where the alkyl group may or may not contain alkylene oxide units; and (d) water to make up the balance;

wherein the proportion by weight (a)/(a)+(b) is 0.4 to 1, and (a)+(b):(c) is 3:1 to 1:2 and the pH of the composition is 6 to 8.5.

2. The liquid detergent composition of claim 1, wherein said component (c) is a surfactant selected from the group consisting of the following (I), (II), (III) and (IV):
   (I) an anionic surfactant selected from the group consisting of aliphatic surfactant and isethionate surfactant;
   (II) an amphoteric surfactant selected from the group consisting of hydroxypropylsulfobetaine and demineralized secondary imidazolinium betaine;
   (III) a nonionic surfactant selected from the group consisting of amine oxide, diethanolamide and alkyl saccharide; and
   (IV) a cationic surfactant selected from the group consisting of $C_{12}$–$C_{16}$ linear monoalkyl quaternary ammonium salt and quaternary ammonium salt having $C_{20}$–$C_{28}$ branched alkyl groups.

3. The liquid detergent composition of claim 1, wherein $R^1$ and $R^2$ are linear alkyl or alkenyl groups.

4. The liquid detergent composition of claim 1, wherein $R^1$ and $R^2$ are linear alkyl groups.

5. The liquid detergent composition of claim 1, wherein the sum of components (a), (b) and (c) is 7–100% by weight based on the total liquid detergent composition.

6. The liquid detergent composition of claim 1, wherein the sum of components (a), (b) and (c) is 15–65% by weight based on the total liquid detergent composition.

7. The liquid detergent composition of claim 1, wherein the proportion by weight (a)/(a)+(b) is 0.50–0.90.

8. The liquid detergent composition of claim 1, in a container having a finger-push-pump.

9. The liquid detergent composition of claim 1, wherein $R^1$ and $R^2$ are linear alkyl or alkenyl groups.

10. The liquid detergent composition of claim 2, wherein $R^1$ and $R^2$ and linear alkyl groups.

11. The liquid detergent composition of claim 2, wherein the sum of components (a), (b) and (c) is 7–100% by weight based on the total liquid detergent composition.

12. The liquid detergent composition of claim 2, wherein the sum of components (a), (b) and (c) is 15–65% by weight based on the total liquid detergent composition.

13. The liquid detergent composition of claim 2, wherein the proportion by weight (a)/(a)+(b) is 0.50–0.90.

14. The liquid detergent composition of claim 2, in a container having a finger-push-pump.

* * * * *

UNITED STATES PATENT AND TRADEMARK OFFICE
CERTIFICATE OF CORRECTION

PATENT NO. : 5,395,542
DATED : March 7, 1995
INVENTOR(S) : Toshio NOZAKI et al It is certified that error appears in the above-identified patent and that said Letters Patent is hereby corrected as shown below:

Column 8, line 46, delete "$R^1$ and $R^2$ and" and insert --$R^1$ and $R^2$ are--.

Signed and Sealed this

Thirteenth Day of June, 1995

*Attest:*

BRUCE LEHMAN

*Attesting Officer*     *Commissioner of Patents and Trademarks*